(12) United States Patent
Babizhayev

(10) Patent No.: US 7,795,203 B2
(45) Date of Patent: Sep. 14, 2010

(54) METHOD FOR TOPICAL TREATMENT OF EYE DISEASE AND COMPOSITION AND DEVICE FOR SAID TREATMENT

(76) Inventor: Mark A. Babizhayev, Ivanovskava 20, Suite 74, Moscow (RU)

( * ) Notice: Subject to any disclaimer, the term of this patent is extended or adjusted under 35 U.S.C. 154(b) by 1636 days.

(21) Appl. No.: 10/480,724

(22) PCT Filed: Sep. 29, 2003

(86) PCT No.: PCT/IB03/04259

§ 371 (c)(1),
(2), (4) Date: Dec. 12, 2003

(87) PCT Pub. No.: WO2004/028536

PCT Pub. Date: Apr. 8, 2004

(65) Prior Publication Data

US 2004/0192647 A1 Sep. 30, 2004

Related U.S. Application Data

(60) Provisional application No. 60/414,357, filed on Sep. 30, 2002.

(51) Int. Cl.
*C07K 5/06* (2006.01)
(52) U.S. Cl. .............................. 514/2; 514/19
(58) Field of Classification Search ........................ None
See application file for complete search history.

(56) References Cited

U.S. PATENT DOCUMENTS

| | | | | |
|---|---|---|---|---|
| 4,248,882 A * | 2/1981 | Sarges et al. | ................. | 514/389 |
| 4,387,232 A | 6/1983 | Eguchi et al. | ................ | 548/344 |
| 4,722,933 A * | 2/1988 | Horn | ........................... | 514/438 |
| 4,738,851 A * | 4/1988 | Schoenwald et al. | ......... | 424/488 |
| 5,428,030 A * | 6/1995 | Miyazaki et al. | ............ | 514/218 |
| 5,496,820 A | 3/1996 | Perälampi | ................ | 514/236.2 |
| 5,866,537 A | 2/1999 | Bianchi | .......................... | 514/2 |
| 6,194,457 B1 * | 2/2001 | Braswell et al. | ............. | 514/547 |
| 6,503,892 B2 * | 1/2003 | Schuman et al. | ............. | 514/152 |
| 2002/0017305 A1 * | 2/2002 | Bagrov et al. | ................ | 128/898 |

FOREIGN PATENT DOCUMENTS

| | | | |
|---|---|---|---|
| JP | 3579063 | | 2/1994 |
| RU | 2100020 | | 12/1997 |
| RU | 2171107 | | 7/2001 |
| WO | 95/10294 | * | 4/1995 |
| WO | WO 95/10294 | | 4/1995 |
| WO | WO 02/060495 A1 | | 8/2002 |

OTHER PUBLICATIONS

Babizhayev et al."N-Acetylcarnosine, A Natural Histidine-Containing Dipeptide, As a Potent Ophthalmic Drug in Treatment of Human Cataracts", 2001, Peptides, vol. 22. pp. 979-994.*
Shichi et al. "Cataract Formation and Prevention", 2004, Expert Opin. Investig. Drugs, vol. 13. pp. 691-701.*
Eye & Vision Center Johns Hopkins Medicine. US news obtained from <http://health.usnews.com/usnews/health/eye_vision/cataract/cat.prevent.htm> obtaind Nov. 8, 2008.*
Clevaland Sight Center, Catarcts. [online] [retrieved on Nov. 8, 2008] Retrived from < http://www.clevelandsightcenter.org/resources/conditions/cataracts.htm >.*
The University of Michigan Kellog Eye Center, Cataract: Definition, Symptoms, and Treatment. [online], [retrieved on Nov. 8, 2008] Retieved from < http://www.kellogg.umich.edu/patientcare/conditions/cataract.html >.*
Myoclinic.com. Cataract: Prevention. [onlin], [retieved on Nov. 8, 2008], Retreived form < http://www.mayoclinic.com/health/cataracts/DS00050/DSECTION=prevention >.*
Babizhayev et al. "N-Acetylcarnosine, a natural histidine-containing dipeptide, as a potent ophthalmic drug in treatment of human cataracts." Peptides, vol. 22, Issue 6, Jun. 2001, pp. 979-994.*
Babizhayev et al.,"Lens Opacity Induced by Lipid Peroxidation Products as a Model of Cataract Associated with Retinal Disease" *Biochimica et Biophysica Acta*, 1004 (1989), 124-133 (Abstract).
Babizhayev et al., "L-Carnosine (beta-alanyl-L-histidine) and Carcinine (beta-alanylhistamine) Act as Natural Antioxidants with Hydroxyl-Radical-Scavenging and Lipid-Peroxidase Activities" *Biochem. J.*, 304, (1994), 509-516 (Abstract).
Babizhayev et al., "Photoprotector and Antioxidant Properties of Histamine-Containing Peptidomimetics in the Photooxidation of Glycyltryptophan" *Biochemistry* (Moscow), 63, (1998), 523-528 (Abstract).
Babizhayev et al., "N Alpha-Acetylcarnosine is a Prodrug of L-Carnosine in Ophthalmic Application as Antioxidant" *Clinica Chemical Acta*, 254, (1996) 1-21 (Abstract).
Babizhayev, "Antioxidant Activity of L-carnosine, a Natural Histidine-Containing Dipeptide in Crystalline Lens" *Biochimica and Biophysica Acta*, 1004, (1989), 363-371 (Abstract).
Boldyrev et al., "The Antioxidative Properties of Carnosine, a Natural Histidine Containing Dipeptide" *Biochem. Intern.*, 15, 1105-13 (1987) (Abstract).
Jackson et al., "Purification and Properties of Human Serum Carnosinase" *Clin. Chim. Acta*, 196, (1991) 193-205 (Abstract).
Lenney et al., "Characterization of Human Tissue Carnosinase" *Biochem. J.*, 228, (1985) 653-660 (Abstract).

(Continued)

*Primary Examiner*—Anish Gupta
(74) *Attorney, Agent, or Firm*—James C. Lydon

(57) ABSTRACT

A method for the prevention or treatment of an eye disease, which includes topically applying to a patient in need of the treatment an aqueous ophthalmic composition which includes N-acetylcarnosine, a N-acetylcarnosine derivative or a pharmacologically acceptable salt of N-acetylcarnosine, in combination with an amount of a cellulose compound or a pharmacologically acceptable salt which is effective to increase intraocular absorption of N-acetylcarnosine or L-carnosine or a derivative of L-carnosine, such as anserine or balenine, in the aqueous humor. A hydrophilic hydrogel contact lens and an ocular polymer insert for topical application of an ophthalmic composition to the eyes of a patient is also disclosed, with the lens or insert containing N-acetylcarnosine, a N-acetylcarnosine derivative or a pharmacologically acceptable salt of N-acetylcarnosine.

16 Claims, No Drawings

OTHER PUBLICATIONS

Babizhayev et al., "The Natural Histidine-Containing Dipeptide N-Acetylcarnosine as an Antioxidant for Ophthalmic use," *Biochemistry* (Moscow) (2000), 65/5: 588-598 (Abstract).

Babizhayev et al., "Efficacy of N-Acetylcarnosine in the Treatment of Cataracts," *Drugs R&D* (2002), 3(2): 87-103 (Abstract).

Babizhayev et al., N-Acetylcarnosine, a Natural Histidine-Containing Dipeptide, as a Potent Ophthalmic Drug in Treatment of Human Cataracts, *Peptides* (2001) 22(6): 979-994 (Abstract).

Murata et al., "Oxidative DNA Damage by Vitamin A and its Derivative via Superoxide Generation," *J Biol Chem* (2000), 275:2003-8 (Abstract).

Teixeira et al., "Use of Antioxidants for the Prophylaxis of Cold-Induced Peripheral Nerve Injury," *Mil Med* (2002), 167: 753-5 (Abstract).

Sharma et al., "Topical Glutathione Therapy in Senile Cataracts. Cataract-III," *Indian J Ophthalmol* (1989), 37(3) : 121-6 (Abstract).

Babizhayev et al., 72 *Mech Ageing Dev.* 1-12 (1993).

Kim et al., 233 *Int. J. Pharm.* 159-67 (2002.

Takano et al., 96 *Nippon Ganka Gakkai Zasshi* 834 (1992).

English translation of Takano et al., 96 *Nippon Ganka Gakkai Zasshi* 834 (1992), previously submitted on Jun. 28, 2007.

\* cited by examiner

SEQUENCE LISTING

```
<160> NUMBER OF SEQ ID NOS: 2

<210> SEQ ID NO 1
<211> LENGTH: 3
<212> TYPE: PRT
<213> ORGANISM: Artificial Sequence
<220> FEATURE:
<223> OTHER INFORMATION: Synthetically generated sequence

<400> SEQUENCE: 1

Arg Gly Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetically generated sequence

<400> SEQUENCE: 2

Arg Gly Asp Ser
1
```

METHOD FOR TOPICAL TREATMENT OF EYE DISEASE AND COMPOSITION AND DEVICE FOR SAID TREATMENT

This application is a U.S. National Stage of International application PCT/IB03/04259, filed Sep. 29, 2003, which claims priority of U.S. provisional application Ser. No. 60/414,357, filed Sep. 30, 2002.

This invention relates to a method of topical treatment and composition for eye diseases. The invention also relates to a device for ophthalmic administration of the composition over an extended period of time.

BACKGROUND OF THE INVENTION

Free radicals and the peroxidative processes caused by them are believed to be one of the causes of the structural and functional degradations of human tissue during aging. It is important to maintain the concentration of natural antioxidant molecules (free radical scavengers) high inside and around the body's various tissues and cells including ocular tissues like the retina, vitreous and the crystalline lens, iris-ciliary body and trabecular meshwork, cornea and conjunctival tissues, and in the body's liquids including the aqueous humor of the anterior eye chamber and in the blood plasma and blood stream in order to supplement organs, tissues and cells and to prevent or minimize the aging processes and related (ocular) pathologies and for longevity. For example, it is believed that in some forms of cataract, especially those associated with retinal disorders, lens clouding is due to the diffusion of toxic products deriving from the oxidation of the lipids from the retina through the vitreous body to the lens. See Babizhayev et al., *Biochimica et Biophysica Acta,* 1004 (1989), 124-133 and references cited therein.

L-Carnosine (β-alanyl-L-histidine) and some derivatives thereof (acetylcarnosine, carcinine, anserine, acetylanserine, balenine, etc.) are known to be among the most important and potent natural antioxidant agents which act as universal antioxidants both in the lipid phase of cellular and biological membranes and in the aqueous environment protecting lipids and water-soluble molecules like proteins (including enzymes), DNA and other essential macromolecules from oxidative damage mediated by reactive oxygen species and lipid peroxides. Babizhayev et al., *Biochem. J.* 304 (1994), 509-516 and references cited therein; Babizhayev et al., *Biochemistry (Moscow)* 63 (1998), 523-528; and Babizhayev et al., *Clinica Chimica Acta* 254 (1996) 1-21.

A striking effect of L-carnosine was demonstrated and has been used in the preventive and therapeutical treatment of cataract. See Babizhayev, *Biochimica and Biophysica Acta,* 1004 (1989), 363-371; and Boldyrev et al., Biochem. Intern. 15, 1105-1113.

However, exogenous carnosine, even when topically administered to the eye, does not accumulate in tissues, but it is excreted with urine or it is preferably destroyed by the enzyme carnosinase, which is present in blood plasma, aqueous humor of the anterior eye chamber, liver and kidney and other tissues, but not in the muscles, Jackson et al., *Clin. Chim. Acta* 196, (1991) 193-206; and Lenney et al., *Biochem. J.* 228 (1985) 653-660 and probably, the lens, Boldyrev et al., "The antioxidative properties of carnosine, a natural histidine containing dipeptide," *Biochem Int* (1987) 15: 1105-1113; Jay et al., "Histidyl derivatives in rabbit lens and their diminution in human cataract," *Meeting Abstr J Physiol Lond* (1990) 420:155.

PCT/EP94/03340 discloses that N-acetylcarnosine is a pro-drug for L-carnosine, and proposes a topical medicant containing N-acetylcarnosine useful in the prevention and therapy of cataract. See also Babizhayev et al., "N-Acetylcarnosine is a prodrug of L-carnosine in ophthalmic application as antioxidant," *Clin Chim Acta* (1996) 254: 1-21; Babizhayev et al., "The natural histidine-containing dipeptide N-acetylcarnosine as an antioxidant for ophthalmic use, *Biochemistry (Moscow)* (2000), 65/5: 588-598; Babizhayev et al., "Efficacy of N-acetylcarnosine in the treatment of cataracts, *Drugs R&D* (2002), 3(2) :87-103; Babizhayev et al., "N-acetylcarnosine, a natural histidine-containing dipeptide, as a potent ophthalmic drug in treatment of human cataracts, *Peptides* (2001) 22(6): 979-994; and Babizhayev et al., "Imidazole-containing peptidomimetic NACA as a potent drug for the medicinal treatment of age-related cataract in humans," *J Anti-Aging Medicine* (2000) 3/1: 43-62.

U.S. Pat. No. 4,387,232 discloses a process for preparing N-acetyl-β-alanyl-L-histidine, which is said to possess a strong controlling action to the cerebrum surroundings. The process reacts histidine and 3-acylaminopropionic acid reactive derivatives such as 3-acetylaminopropionic chloride, and the tertiary amine salt of 3-acetylaminopropionic acid and sulfuric acid mixed anhydride.

U.S. Pat. No. 5,866,537 discloses an oral composition containing the combination of carnosine and branched amino acids leucine, isoleucine and valine. The composition is said to induce a prolonged antioxidant activity in comparison to carnosine alone. Carnosine derivatives such as homocarnosine, acetylcarnosine, anserine, acetylanserine and ofidine, and/or their biologically acceptable inorganic and organic salts, and/or acyl derivatives may be used in place of carnosine.

Carboxymethylcellulose sodium salt is widely used in oral and topical pharmaceutical formulations primarily for its viscosity-increasing properties. Viscous aqueous solutions are used to suspend powders intended for either topical application or oral and parenteral administration. See Hussain et al., "Injectable suspensions for prolonged release nalbuphine," *Drug Dev Ind Pharm* (1991), 17: 67-76. Carboxymethylcellulose sodium may also be used as a tablet binder and disintegrant, Khan K A et al., "Evaluation of different viscosity grades of sodium carboxymethylcellulose as tablet disintegrants," *Pharm Acta Helv* (1975), 50: 99-102, and to stabilize emulsions, Oza et al., "Microcrystalline cellulose stabilized emulsions," *J Disper Sci Technol* (1986), 7(5): 543-561. Higher concentrations, usually 3-6%, of the medium viscosity grade is used to produce gels which can be used as the base for pastes. Carboxymethylcellulose sodium salt is additionally one of the main ingredients of self-adhesive ostomy, wound care, and dermatological patches where it is used to absorb wound exudates or transepidermal water and sweat. Carboxymethylcellulose sodium salt is also used in cosmetics, toiletries, incontinence, personal hygiene, and food products. See Mombellet et al., "Sodium carboxymethylcellulose toothpaste," *Mfg Chem* 1088; 59(11): 47,49, and 52.

U.S. Pat. No. 6,194,457 discloses the use of lubricants such as sodium carboxymethylcellulose in a liquid eye drop composition which contains reduced glutathione, vitamin A and vitamin E, as well as one or more of zinc sulfate, boric acid and potassium as buffering agents. The composition also may contain a preservative such as benzyl alcohol. The composition is used in a method of treating eyes for the alleviation of irritations and/or dryness, as well as for the prevention and treatment of cataracts.

N-acetylcarnosine per se can act as a very weak antioxidant and vitamin A and its derivatives can possess pro-oxidant action via superoxide generation, Murata et al., "Oxidative DNA damage by vitamin A and its derivative via superoxide generation" *J Biol Chem* (2000); 275:2003-8. Besides, the vitamin E molecule with branched hydrocarbon skeleton completely inhibits the deacetylation of the amino acid derivative product, Teixeira et al., "Use of antioxidants for the prophylaxis of cold-induced peripheral nerve injury," *Mil Med* (2002);167:753-5 and reduced glutathione promotes the formation of posterior subcapsular cataracts when applied in the ophthalmic compositions, Sharma et al. "Topical glutathione therapy in senile cataracts. Cataract-III." *Indian J Ophthalmol* (1989); 37(3):121-6.

An object of the present invention is to provide an ophthalmic composition containing N-acetylcarnosine which is safe and which is completely converted into L-carnosine in the aqueous humor.

Another object of the invention is to provide an ophthalmic omposition which can significantly increase the bioavailability of N-acetylcarnosine/L-carnosine in the aqueous humor.

BRIEF SUMMARY OF THE INVENTION

The inventor has unexpectedly discovered that the biotransformation or metabolization of N-acetylcarnosine into L-carnosine upon the topical ocular administration of the N-acetylcarnosine compound into the conjunctival sac is increased by the presence of a cellulose compound such as carboxymethylcellulose. Accordingly, in one aspect, the present invention relates to a method for the prevention or treatment of an eye disease, comprising topically applying to a mammal in need of said treatment an aqueous ophthalmic composition comprising N-acetylcarnosine, a N-acetylcarnosine derivative, or a pharmacologically acceptable salt of N-acetylcarnosine, in combination with an amount of a cellulose compound or its pharmacologically acceptable salt which is effective to increase intraocular absorption of N-acetylcarnosine and/or L-carnosine or a L-carnosine derivative.

In another aspect, the present invention relates to an aqueous ophthalmic composition comprising N-acetylcarnosine, a N-acetylcarnosine derivative, or a pharmacologically acceptable salt thereof in combination with an amount of a cellulose compound or its pharmacologically acceptable salt which is effective to increase intraocular absorption of N-acetylcarnosine and/or L-carnosine, or a L-carnosine derivative by a mammal upon ophthalmic application of the composition.

In yet another aspect, the present invention relates to a device for topical application of an ophthalmic composition to the eyes of a patient, comprising a hydrophilic hydrogel contact lens or a polymeric ocular insert, the lens or ocular insert containing N-acetylcarnosine, a N-acetylcarnosine derivative or a pharmacologically acceptable salt of N-acetylcarnosine.

In still another aspect, the present invention relates to a method of treatment of glaucoma comprising topically applying to a mammal in need of said treatment an aqueous ophthalmic composition comprising N-acetylcarnosine or L-carnosine and/or taurine or a derivative thereof, or a pharmacologically acceptable salt thereof, in combination with an active principle having β- and/or α-adrenoreceptor blocking activity and/or a prostaglandin derivative and an amount of a cellulose compound or its pharmacologically acceptable salt which is effective to increase intraocular absorption of the N-acetylcarnosine or L-carnosine and/or taurine or derivative thereof.

DETAILED DESCRIPTION OF THE PREFERRED EMBODIMENTS

Mammals which can be treated according to the method of the invention include humans, canines, cats, rabbits and equines.

By "eye diseases" it is meant eye disorders including cataract, open-angle primary glaucoma, corneal disorders, presbyopia, computer vision syndrome, eye strain, ocular inflammation, blurred vision, dry eye syndrome, retinal diseases, vitreous opacities and lesions, complications of diabetes mellitus and other systemic diseases.

N-acetylcarnosine can be prepared by acetylation of carnosine using conventional procedures well known to those skilled in the art. Thus, for example, L-carnosine can be acetylated with acetic anhydride in 2N-NaOH and treated with an ion-exchange resin such as SK-1B. After elution with 1N-ammonia, the eluate is concentrated. Treatment with acetic acid followed by isopropyl alcohol yields crystals. Recrystallization from a water-isopropyl alcohol solution gives pure N-acetylcarnosine crystals:

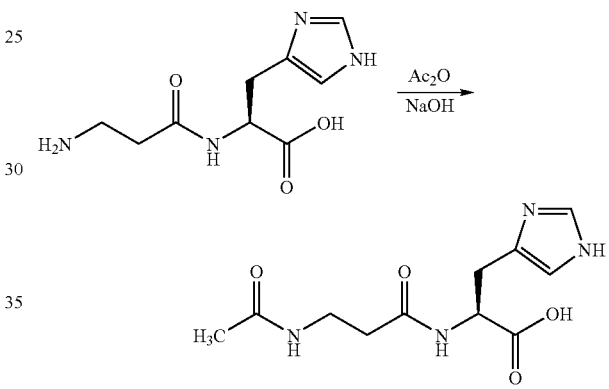

Alternatively, N-acetylcarnosine can be prepared by acetylating β-alanine by any known method, for example with acetic anhydride in an alkaline medium. The resulting N-acetyl-β-alanine may be derivatized with pentafluorophenyl, according to the method described by M. Bodansky in the "Practice of Peptide Synthesis," (1984), incorporated by reference herein, to give N-acetyl-β-alanine pentafluorophenyl ester. In the subsequent step, the ester is reacted with histidine methyl ester to give the dipeptide, thereafter the final product is obtained by hydrolysis of the ester.

"N-acetylcarnosine derivative" means carcinine (β-alanyl-histamine), anserine (β-alanyl-1-methyl-L-histidine), homocarnosine (β-amino-butyryl-L-histidine), ophidine (balenine (β-alanyl-3-methyl-L-histidine)) and their N-acetylated and acyl-derivative compounds. These compounds can be prepared by procedures well known to those of ordinary skill in the art.

Pharmacologically acceptable salts of N-acetylcarnosine and its derivatives may be any pharmacologically compatible inorganic and organic salts thereof. Again, one of ordinary skill in the art can prepare such salts using well-known procedures.

The N-acetylcarnosine, N-acetylcarnosine derivative or pharmacologically acceptable salt of N-acetylcarnosine must be extremely pure when used for ophthalmic application. More particularly, the N-acetylcarnosine, its derivative or pharmacologically acceptable salt should have a heavy metals content of less than 10 ppm. Chromatographic purification of N-acetylcarnosine can be performed using a silica gel column.

The N-acetylcarnosine, its derivative or its salt may be present in the aqueous ophthalmic composition in an amount ranging from 0.5 to less than 3.0% by weight, preferably 0.5 to 2%, based on the total weight of the composition.

The aqueous ophthalmic composition also contains a cellulose compound or a pharmacologically acceptable salt thereof. "Cellulose compound" means any polysaccharide which is capable of increasing the intraocular absorption of N-acetylcarnosine, a N-acetylcarnosine derivative or pharmacologically acceptable salt, and/or carnosine. The cellulose compound is preferably at least one member selected from carboxymethylcellulose, carboxypolymethylene and polyvinylpyrrolidone, with carboxymethylcellulose being most preferred.

Pharmacologically acceptable salts of cellulose include carboxymethylcellulose sodium and sodium cellulose glycolate. The USP describes carboxymethylcellulose sodium as the sodium salt of a polycarboxymethyl ether of cellulose. A typical molecular weight is 90,000-700,000.

Cellulose compounds suitable for use in the present invention are commercially available in various forms from various manufacturers. Benzene-free carboxypolymethylene is commercially available under the trademark CARBOMER 980. Similarly, polyvinylpyrrolidone is commercially available under the trademark KOLLIDON K17.

The ophthalmic composition should contain the cellulose compound, or its pharmacologically acceptable salt, in an amount which is effective to increase intraocular absorption of N-acetylcarnosine and/or a derivative thereof when the composition is topically applied to the eye. By "intraocular absorption" it is meant absorption in the aqueous humor of the anterior eye chamber of a mammal. N-acetylcarnosine is converted into L-carnosine during its passage throught the cornea into the aqueous humor. Derivatives of N-acetylcarnosine (except N-acetylcarcinine) are believed to undergo similar metabolization, gradually. Thus, N-acetyl-anserine can be converted into anserine during its passage through the cornea into the aqueous humor.

An illustrative amount of the cellulose compound ranges from 0.1% to 0.5% by weight, preferably 0.2 to 0.4%, based on the total weight of the composition.

Without intending to be bound by theory, the inventor currently believes that N-acetylcarnosine is metabolized or otherwise converted into carnosine during its passage through the cornea into the aqueous humor of the anterior eye of the mammal. It is believed that L-carnosine then enters the lens without associated carnosinase activity and acts as a pure antioxidant/anti-cataract remedy reversing and/or preventing cataracts and other ophthalmic disorders which have a component of oxidative stress in their genesis. The cellulose compound is believed to increase this metabolization. The inventive formulation, i.e., the combination of the N-acetylcarnosine and cellulose compound, thus serves. to efficiently release L-carnosine in the aqueous humor over time.

In a preferred embodiment, the ophthalmic composition also contains a compound having combined β- and α-adrenoceptor blocking activity, such as, for example, 3-methyl-5-[2-(3-tert-butylamino-2-hydroxypropoxy-phenoxymethyl]-1,2,4-oxadiazole hydrochloride. This compound, also known as (±)-1-(tert-Butylamino)-3-[2-(3-methyl-1,2,4-oxadiazol-5-ylmethoxy)phenoxy]-2-propanol hydrochloride or (±)-5-[2-(3-tert-Butylamino-2-hydroxypropoxy)phenoxymethyl]-3-methyl-1,2,4-oxadiazole hydrochloride, has the following formula:

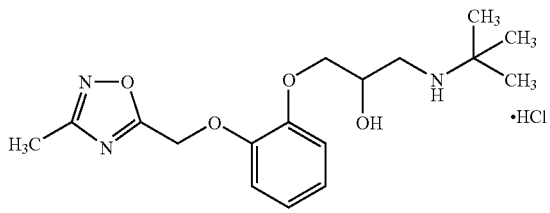

$C_{17}H_{25}N_3O_4 \cdot HCl$    Mol wt: 371.86

The inclusion of an α,β-adrenoreceptor blocking compound is believed to enhance the composition's utility in the treatment of glaucoma by decreasing the intraocular pressure and stimulating the outflow facility of the aqueous humor.

The ophthalmic composition of the present invention may also contain a peptide containing Arg-Gly-Asp (SEQ ID NO: 1), such as N-acetyl-Arg-Gly-Asp-Ser peptide (N-acetyl-RGDS peptide) (SEQ ID NO: 2) to treat eye disease, particularly primary open-angle glaucoma (POAG) and ocular hypertension (OH).

Without intending to be bound by theory, the inventor currently believes that RGD-containing peptides, and/or their pharmacologically acceptable salts, are efficacious for the therapeutical and surgical treatment of primary open-angle glaucoma (POAG) and ocular hypertension (OH). In a clinical study 0.1% N-Acetyl-RGDS taken topically twice daily effectively reduced intraocular pressure (IOP) and was well tolerated in patients with POAG and OH. It was more effective in reducing IOP than 0.5% timolol taken twice daily. The effect of 0.1% N-Acetyl-RGDS on outflow facility, as studied by tonography, was striking providing a significant increase to 26-33%. The cleansing activity of Acetyl-RGDS is accompanied by increase in trabecular outflow facility which is different from that of other drugs (pilocarpine) previously shown in patients with POAG and OH. The clinical significance and mechanism of IOP reduction by N-Acetyl-RGDS are related with the cleansing effect of N-Acetyl-RGDS on extracellular matrix proteins and plaque material in trabecular meshwork to reduce the outflow resistance in the eyes of patients with POAG and OH. It is believed N-Acetyl-RGDS is also suitable to treat secondary cataracts and vitreoproliferative disorders.

The N-acetyl RGDS peptide or its salt may be present in the aqueous ophthalmic composition in an amount ranging from 0.05 to less than 0.5% by weight, preferably 0.05 to 0.25%, most preferably 0.1% based on the total weight of the composition.

The ophthalmic composition of the present invention can also contain conventional additives if these additives do not inhibit the biotransformation of N-acetylcarnosine into carnosine during its passage through the cornea into the aqueous humor. For example, antioxidants such as vitamin A and vitamin E can be added to the ophthalmic composition to increase the antioxidant potential. Similarly, lubricants such as polyoxyethylene fatty acid esters can be included in the ophthalmic composition in conventional amounts. Illustrative esters include polyoxyethylene sorbitan monolaurate, polyoxyethylene sorbitan monostearate, polyoxyethylene sorbitan monooleate and polyoxyethylene sorbitan tristearate. These esters are commercially available under the Polysorbate trademark. They may be advantageously employed in an amount of about 0.2% by weight of the total composition.

Preservatives conventionally used in eye drop solutions may be included in the composition of the present invention if they do not inhibit the biotransformation of N-acetylcarnosine into carnosine during its passage through the cornea into the aqueous humor. Suitable preservatives include benzyl alcohol and para-amino-benzoic acid.

Lactoferrin and/or albumin may be included in the composition of the present invention especially for the treatment of dry eye syndrome and to treat the conditions of the eye during the wear of contact lenses. Typically, these ingredients are used in the dosages they are present in the natural tear fluid. For example, the typical dose of human lactoferrin should be 1.7±0.2 mg/ml.

Glycerine may also be optionally included in an amount effective to prevent excessive corneal hydration (oedema) and ocular irritation.

The ophthalmic composition can also include an amount of taurine (2-aminoethanesulfonic acid) or a derivative thereof, which is effective to relax ocular muscles, and/or L-carnosine, which is effective to inhibit the inflammatory effect of prostaglandins.

The ophthalmic composition can also include at least one carnosinase inhibitor, preferably selected from leucine, isoleucine, valine and β-alanine. The purpose of the carnosine inhibitor is to retard or stabilize hydrolysis of carnosine in the aqueous humor.

The pH of the aqueous ophthalmic composition should be in a range of from 6.0 to 6.8, preferably from 6.3 to 6.8. A buffer system may be added to maintain the pH at a desired value. An illustrative buffer system is sodium or potassium borate in combination with sodium or potassium bicarbonate.

The aqueous composition of the present invention can be topically applied to the eye of a mammal for the prevention or treatment of an eye disease. Accordingly, the composition may be in the form of a solution, an emulsion, or a viscous gel.

For the treatment or prevention of dry eye syndrome and cataracts, the ophthalmic composition may conveniently be in the form of a moderately viscous aqueous solution. A suitable formulation advantageously contains the following ingredients:

N-Acetylcarnosine 1%
Carboxymethylcellulose sodium (lubricant) 0.3%
Glycerine (lubricant) 1%,
Buffers: Potassium Borate, Potassium Bicarbonate
Preservative: Purified Benzyl Alcohol.
Sterile Water (ophthalmic grade solution pH 6.3 to 6.5)

The method of the present invention for the prevention or treatment of an eye disease includes topically applying to a mammal in need of said treatment an aqueous ophthalmic composition comprising N-acetylcarnosine, a N-acetylcarnosine derivative, or a pharmacologically acceptable salt of N-acetylcarnosine, in combination with an amount of a cellulose compound which is effective to increase intraocular absorption of N-acetylcarnosine, and/or L-carnosine and/or a L-carnosine derivative, in the aqueous humor.

The patient may apply 1 or 2 drops to each eye 1-4 times a day or as directed by a physician. For the proper application of drops, the patient may lean his or her head back and look up. Do not blink or reopen the eye for 60 seconds after application. Repeat this procedure, if a second drop is applied. Closing the eye allows each drop to be absorbed into the eye tissue. Blinking, even one or two times, will pump most of the solution out of the eye. The patient may lie or use a tilt-back chair if the patient has a neck problem or is otherwise adverse to looking up.

The ophthalmic composition may be applied discretely one to four times per day as illustrated above. Alternatively, the active ingredient may be continuously applied over time by means of a hydrophilic hydrogel contact lens or ocular polymer insert which contains N-acetylcarnosine, a N-acetylcarnosine derivative, or a pharmacologically acceptable salt of N-acetylcarnosine.

Yet another advantage of the present invention is that systemic absorption of N-acetylcarnosine and/or carnosine is increased through the microvessels of the conjunctival and lid mucosal tissues because the cellulose compound increases the time of persistence of N-acetylcarnosine in the conjunctival sac. More particularly, N-acetylcarnosine appears in blood plasma within 30 min of its topical administration to the eye with carboxymethylcellulose. The half time of decay of N-acetylcarnosine in plasma is about 150 min or more according to pharmacokinetic studies. N-acetylcarnosine is a substrate of carnosinase similar to L-carnosine but is highly resistant to hydrolysis with carnosinase. Accordingly, once in blood plasma N-acetylcarnosine can act as a compettitve saturating inhibitor of carnosinase, which is very helpful to protect L-carnosine from hydrolysis during concomitant oral administration of L-carnosine as an anti-aging therapy.

The inventor also believes that N-aceytlcarnosine has utility for cosmetic, skin, other personal care uses and health applications. For example, a formulation adapted for nasal application of N-acetylcarnosine and carboxymethylcellulose is believed to enhance bioavailability and pharmacodynamics of N-acetylcarnosine.

Illustrative Formulations

The formulations listed below are set forth for illustrative purposes only, and should not be used to limit the proper construction of the claims in any manner whatsoever.

1. Aqueous Ophthalmic Composition for Treatment of Eye Disease

An illustrative formulation for treatment of eye disease is set forth below:

| Formulation No. 1 | |
| --- | --- |
| Deionized Water | 970 grams |
| Glycerine, 1.0% | 13 grams |
| N-acetylcarnosine, 1.0% | 10 grams |
| Carboxymethylcellulose, 0.3% | 3 grams |
| Benzyl Alcohol, 0.3% | 3 grams |
| Potassium Borate | 7.9 grams* |
| Potassium Bicarbonate | 3.4 grams* |
| | 1,010.3 |

*or what is necessary to adjust the pH to 6.3-6.5.

2. Aqueous Ophthalmic Composition for Treatment of Eve Disease

Illustrative Formulation No. 2 differs from illustrative Formulation No. 1 by the substitution of phenyl-ethyl alcohol for benzyl alcohol and by the replacement of the phosphate buffers with corresponding sodium buffers:

| Formulation No. 2 | |
|---|---|
| Deionized Water | 970 grams |
| Glycerine, 1.0% | 13 grams |
| N-acetylcarnosine, 1.0% | 10 grams |
| Carboxymethylcellulose, 0.3% | 3 grams |
| Phenyl-ethyl Alcohol, 0.3% | 3 grams |
| Sodium Borate | 7.9 grams* |
| Sodium Bicarbonate | 3.4 grams* |
| | 1,010.3 |

*or what is necessary to adjust the pH to 6.3-6.5.

3. Aqueous Ophthalmic Composition for Treatment of Eye Disease

Illustrative Formulation No. 3 differs from illustrative Formulation No. 1 by the replacement of carboxymethylcellulose with Carbomer 980:

| Formulation No. 3 | |
|---|---|
| Deionized Water | 970 grams |
| Glycerine, 1.0% | 13 grams |
| N-acetylcarnosine, 1.0% | 10 grams |
| Carbomer 980 | 2 grams |
| Benzyl Alcohol, 0.3% | 3 grams |
| Potassium Borate | 7.9 grams* |
| Potassium Bicarbonate | 3.4 grams* |
| | 1,009.3 |

*or what is necessary to adjust the pH to 6.3-6.5.

4. Aqueous Ophthalmic Composition for Treatment of Glaucoma

An illustrative formulation for treatment of an eye disease, particularly glaucoma, is set forth below:

| Formulation No. 4 | |
|---|---|
| Deionized Water | 970 grams |
| Glycerine, 1.0% | 13 grams |
| N-acetyl-RGDS, 0.1% | 1 gram |
| Carboxymethylcellulose, 0.3% | 3 grams |
| Benzyl Alcohol, 0.3% | 3 grams |
| Potassium Borate | 7.9 grams* |
| Potassium Bicarbonate | 3.4 grams* |
| | 1,001.3 |

*or what is necessary to adjust the pH to 6.3-6.5.

5. Aqueous Ophthalmic Composition for Treatment of CVS

An illustrative formulation for treatment of an eye disease, particularly computer vision syndrome (CVS), is set forth below:

| Formulation No. 5 | |
|---|---|
| Deionized Water | 970 grams |
| Glycerine, 1.0% | 13 grams |
| N-acetylcarnosine, 1.0% | 10 grams |
| Taurine, 4% | 40 grams |
| p-aminobenzoic acid, 0.007% | 0.07 grams |
| Carboxymethylcellulose, 0.3% | 3 grams |
| Benzyl Alcohol, 0.3% | 3 grams |
| Potassium Borate | 7.9 grams* |
| Potassium Bicarbonate | 3.4 grams* |
| | 1,050.37 |

*or what is necessary to adjust the pH to 6.3-6.5.

6. Aqueous Ophthalmic Composition for Treatment of CVS

Illustrative Formulation No. 6 differs from illustrative Formulation No. 5 by the replacement of N-acetylcarnosine with L-carnosine:

| Formulation No. 6 | |
|---|---|
| Deionized Water | 970 grams |
| Glycerine, 1.0% | 13 grams |
| L-carnosine, 1.0% | 10 grams |
| Taurine, 4% | 40 grams |
| p-aminobenzoic acid, 0.007% | 0.07 grams |
| Carboxymethylcellulose, 0.3% | 3 grams |
| Benzyl Alcohol, 0.3% | 3 grams |
| Potassium Borate | 7.9 grams* |
| Potassium Bicarbonate | 3.4 grams* |
| | 1,050.37 |

*or what is necessary to adjust the pH to 6.3-6.5.

EXAMPLES

The Examples are illustrative only, and should not be used to limit the scope of the claims in any manner whatsoever.

Example 1

Biotransformation in the Rabbit Eye

Several of the illustrative formulations disclosed above were topically applied to the right eye of rabbits, while corresponding controls consisting of the solution vehicle without N-acetylcarnosine were topically applied to the left eye of the rabbit. Samples of aqueous humor were taken from each eye thirty minutes after application and analyzed for N-acetylcarnosine and carnosine concentrations against standards.

1.1 Experimental and Analytical Procedures

Experimental procedures were conducted substantially as described by Babizhayev et al., "N-acetylcarnosine is a prodrug of L-carnosine in ophthalmic application as antioxidant", *Clinica Chimica Acta* 254 (1996) 1-21.

Thirty grey Chinchilla rabbits (male, 60 eyes) aged 3-4 months weighing 2-3 kg were used. Animal experiments conformed to the guidelines of the ARVO Resolution on the Use of Animals in Research. Thirty minutes prior the ocular incision right eyes of rabbits were instilled with 2 drops of the testing formula and then after 1 min delay the same eyes were instilled with another 2 drops of the same ophthalmic solution and the left eyes of the animals were similarly instilled with the corresponding formula solution representing their vehicles.

Surgical Procedures

Topical anaesthesia of the rabbit eyes was performed 25 min after instillation of the ophthalmic solutions with instillations of 4% lidocaine hydrochloride solution eye drops (three times with 1 drop at 1.5-2.0 min intervals). The eye drops of 4% lidocaine hydrochloride contain benzaltonium chloride preservative. When ocular anaesthesia was achieved, the lids were extended and fixed with the lid-holder and the ocular bulb was fixed by tweezers in the area of the inferior rectus muscle. A stab incision was performed transcorneally 1.0-2.0 mm from the limbus in the temporal superior quadrant. Aqueous humor (0.1-0.2 ml) was aspirated from the anterior chamber of a rabbit eye with 25-gauge needle connected to an insulin syringe and immediately introduced into an Eppendorf tube with addition of ethanol (0.2 ml), keeping the sample on ice before extraction.

Extraction of Imidazoles from Aqueous Humor

Portions of aqueous humor were added to ethanol as above and thoroughly mixed (20° C., 15 min). Extracts were centrifuged (2000×g, 15 min) and the supernatants removed. Samples were frozen in the gradient of temperatures to −70° C. and lyophilized using the JOAN apparatus (France). The lyophilized residue was dissolved in 1 ml of 0.1 M $Na_2 HPO_4$ (pH 2.1 adjusted with 85% phosphoric acid) and filtered through a membrane filter having 0.22 μm pores directly prior to the analysis.

Analytical HPLC

Reverse phase analytical HPLC was performed using a Breeze chromatography system (USA), equipped with a Waters 2487 Dual λ absorbance detector, a Symmetry 300 $C_{18}$ column (250×4.6 mm), 5 μm (Waters), loop 20 μl. The column was eluted isocratically at 30° C. with 0.1 M $Na_2 HPO_4$ (pH 2.1) over 25 min at a flow rate of 1.0 ml/min. Eluates were monitored for absorbance at 210 nm.

Quantitative determination of L-carnosine and N-acetylcarnosine in the samples was undertaken using the technique of external standard according to the area of the peak and linear extrapolation. Statistical significance was evaluated by the unpaired Student's t-test and P=0.05 was taken as the upper limit of significance.

L-carnosine and N-acetylcarnosine external standards were prepared by weighing of the dry material using the analytical balance Mettler Toledo (accuracy 0.00004) and were dissolved in the phosphate buffer 0.1 M $Na_2 HPO_4$ (pH 2.1). The standards were prepared by dissolution of initial solutions by 100 fold using the phosphate buffer 0.1 M $Na_2 HPO_4$ (pH 2.1).

1.2 Results

As shown in Table 1 below, the concentration of carnosine in the aqueous humor was distinctly increased upon topical application to the rabbit eye of an ophthalmic composition which contained 1% N-acetylcarnosine.

TABLE 1

| Formulation | C/NAC ratio | Number of Rabbit Eyes Treated |
|---|---|---|
| 1 | 6.64 ± 0.06 | 8 |
| 2 | 1.94 ± 0.12 | 5 |
| 3 | 1.98 ± 0.05 | 5 |
| Control 1 | 1.03 ± 0.51 | 5 |
| Control 2 | 1.45 ± 0.03 | 5 |

Control formulation No. 1 contained only N-acetylcarnosine dissolved in a buffered solution:

| Control Formulation No. 1 | |
|---|---|
| Deionized Water | 970 grams |
| N-acetylcarnosine, 1.0% | 10 grams |
| Potassium Borate | 7.9 grams* |
| Potassium Bicarbonate | 3.4 grams* |
| | 991.3 |

*or what is necessary to adjust the pH to 6.3-6.5.

Control formulation No. 2 contained N-acetylcarnosine and phenyl-ethyl alcohol dissolved in a buffered solution:

| Control Formulation No. 2 | |
|---|---|
| Deionized Water | 970 grams |
| N-acetylcarnosine, 1.0 | 10 grams |
| Phenyl-ethyl alcohol, 0.3% | 3 grams |
| Potassium Borate | 7.9 grams* |
| Potassium Bicarbonate | 3.4 grams* |
| | 991.3 |

*or what is necessary to adjust the pH to 6.3-6.5.

The average data presented for administration of N-acetylcarnosine in different formulas with or without lubricant indicate that the released L-carnosine is accumulated at the greater extent in relation to N-acetylcarnosine in the aqueous humor after the treatment with Formulation 1 in comparison to other formulations.

Example 2

Clinical Study

Illustrative Formula 1 was topically applied to the eyes of five human volunteers to evaluate the change in short-term glare sensitivity.

2.1 Clinical Design

The five subjects had no distinct signs of cataracts, but had signs of presbyopia consistent with their age:

TABLE 2

| Subject No. | Gender | Age |
|---|---|---|
| 1 | Male | 54 |
| 2 | Female | 65 |
| 3 | Male | 42 |
| 4 | Female | 57 |
| 5 | Male | 60 |

Best Corrected Visual Acuity

Visual acuity testing was performed to obtain the best distant decimal visual acuity with optical correction when required. Visual acuity was measured by projection screens (Carl Zeiss) with acuity lines in the following LogMar (log of the minimum angle of resolution) steps: 0.1 to 0.4 in 0.05 steps, 0.4 to 1.0 in 0.1 log unit steps. The best correction for nearness was also envisaged in this clinical study.

Best Corrected Glare Disability

The contrast diminishing effect of glare is increased in patients with opaque intraocular media, and vicual acuity is reduced.

An optical instrument and method for measuring susceptibility to glare of a human vision system using the halometer technique is described in U.S. Pat. No. 6,007,203, the disclosure of which is hereby incorporated by reference in its entirety. Briefly, the halometer technique is based on the measurements of a glare radius (defined as a target image projection for the light scatter vector named indicatrix of light scatter $I=I_o\cos^2\omega$) which appears when the glare source is activated. The patient is requested to cover the eye not being tested and asked to recognize the target (changed optotypes: figures or Landoldt rings) during illumination of the eye with a glare source. The luminous target was shifted right and left upon the positioning to glare source and a patient was examined on the ability to nominate the optotypes in response to inquiries. The resulting target-glare source distance measured (mm) in case a patient could just identify an optotype was assessed as a threshold measure of glare sensitivity in the tested eye. After the primary threshold measure of the glare radius on the scale is made, the clinician shifts the indicator laterally from the glare source until the examined patient starts to distinguish the optotypes again correctly, and notes the true threshold distance value. Because a patient cannot recognize an optotype target when it enteres into the glare area ("halos") the significant change of the glare radius (sensitivity) value indicates the changes in intensity of intraocular light scattering (lens clarity). The significant increase and decrease of the glare radius to indicate worsening or improvements is usually a reading of 4 mm with a SE (n=4)±1 mm that indicates changes in lens clarity toward opacification (increased light scattering) and clarification (decreased light scattering). The input of the light scatter wavelength was estimated using the coloured (red or green) modes of the target. Data from the left and right eyes were analyzed separately.

Glare sensitivity measurements were performed using a green target to estimate the change in the optical media clarity upon the ophthalmic application of Illustrative Formulation No. 1.

Background measurements of glare sensitivity were undertaken in both eyes.

The instillation of Formulation No. 1 was performed once (one drop) per visit to the eye according to the double blind method and a placebo solution was instilled in the contralateral eye of the involved subject.

Measurements of glare sensitivity in both eyes were conducted in both eyes after 40 min of application of the formulations.

2.1 Results

Table 3 sets forth the subjects' glare sensitivity measurements with best correction before and 40 minutes after topical application of Illustrative Formulation No. 1 or the placebo formulation:

TABLE 3

| Subleat | Background | | Placebo | | Formulation | |
|---|---|---|---|---|---|---|
|  | OD | OS | OD | OS | OD | OS |
| 1 | 5 mm | 5 mm |  |  | 5 mm | 3-4 mm |
| 2 | 1 mm | 4 mm | 2 mm |  |  | 2 mm |
| 3 | 0 mm | 4 mm | 0-1 mm |  |  | 3 mm |
| 4 | 7 mm | 0-1 mm | 7 mm |  | 4 mm |  |
| 5 | 9 mm | 8 mm | 10 mm |  |  | 5 mm |

There was a tendency towards improvement of glare sensitivity in the adult patients upon application of Illustrative Formulation No. 1.

Topical short-term administration of Illustrative Formulation No. 1 to the eye was very well tolerated, with no ocular or systemic adverse effects, no hyperaemia of conjunctival vessels, and no signs of allergy or other toxic manifestations. No treated eyes demonstrated a worsening of vision.

I claim:

1. A method for the treatment of an eye disease, comprising topically applying to a mammal in need of said treatment an aqueous ophthalmic composition comprising N-acetylcarnosine, a N-acetylcarnosine derivative or a pharmacologically acceptable salt of N-acetylcarnosine, in combination with carboxymethylcellulose or its pharmacologically acceptable salt, in an amount effective to increase intraocular absorption of L-carnosine or a L-carnosine derivative into the aqueous humor, wherein said N-acetylcarnosine is present in an amount ranging from 0.5% to 2% by weight of the composition.

2. The method of claim 1, wherein a pharmacologically acceptable salt of said cellulose compound is carboxymethylcellulose sodium salt.

3. The method of claim 1, wherein said aqueous ophthalmic composition comprises at least one preservative selected from the group consisting of benzyl alcohol and para-amino-benzoic acid.

4. The method of claim 1, wherein said aqueous ophthalmic composition comprises at least one polyoxyethylene fatty acid ester.

5. The method of claim 4, wherein said polyoxyethylene fatty acid ester is a member selected from the group consisting of polyoxyethylene sorbitan monolaurate, polyoxyethylene sorbitan monostearate, polyoxyethylene sorbitan monooleate and polyoxyethylene sorbitan tristearate.

6. The method of claim 1, wherein said aqueous ophthalmic composition comprises at least one vitamin compound selected from the group consisting of vitamin A and vitamin E.

7. The method of claim 1, wherein said aqueous ophthalmic composition comprises glycerine in an amount effective to prevent excessive corneal hydration (oedema) or ocular irritation.

8. The method of claim 1, wherein said cellulose compound is carboxymethylcellulose, present in an amount ranging from 0.2% to 0.4% by weight of the composition.

9. The method of claim 1, wherein said aqueous ophthalmic composition comprises at least one buffer in an amount effective to maintain a pH of said composition in a range of from 6.0 to 6.8.

10. The method of claim 9, wherein said pH ranges from 6.3 to 6.8.

11. The method of claim 9, wherein said aqueous ophthalmic composition comprises sodium or potassium borate in combination with sodium or potassium bicarbonate.

12. The method of claim 1, wherein said eye disease is a member selected from the group consisting of cataract, open-angle primary glaucoma, corneal disorders, presbyopia, computer vision syndrome, eye strain, ocular inflammation, blurred vision, dry eye syndrome, retinal diseases, vitreous opacities and lesions, and complications of diabetes mellitus and systemic disorders.

13. The method of claim 1, wherein said mammal is selected from the group consisting of humans, canines, cats, rabbits and equines.

14. The method of claim 1, wherein said aqueous ophthalmic composition comprises Formulation No. 1:

| | | |
|---|---|---|
| Deionized Water | 970 | grams, |
| Glycerine, | 13 | grams, |
| N-acetylcarnosine, | 10 | grams, |
| Carboxymethylcellulose, | 3 | grams, |
| Benzyl Alcohol, | 3 | grams, |
| Potassium Borate | 7.9 | grams or the amount necessary to adjust the pH to 6.3-6.5, |
| Potassium Bicarbonate | 3.4 | grams or the amount necessary to adjust the pH to 6.3-6.5. |

15. The method of claim 1, wherein said aqueous ophthalmic composition comprises Formulation No. 2:

| | | |
|---|---|---|
| Deionized Water | 970 | grams, |
| Glycerine, | 13 | grams, |
| N-acetylcarnosine, | 10 | grams, |
| Carboxymethylcellulose, | 3 | grams, |
| Phenyl-ethyl Alcohol, | 3 | grams, |
| Sodium Borate | 7.9 | grams or the amount necessary to adjust the pH to 6.3-6.5, |
| Sodium Bicarbonate | 3.4 | grams or the amount necessary to adjust the pH to 6.3-6.5. |

16. The method of claim 1, wherein said aqueous ophthalmic composition comprises Formulation No. 5:

| | | |
|---|---|---|
| Deionized Water | 970 | grams, |
| Glycerine, | 13 | grams, |
| N-acetylcarnosine, | 10 | grams, |
| Taurine, | 40 | grams, |
| p-aminobenzoic acid, | 0.07 | grams, |
| Carboxymethylcellulose, | 3 | grams, |
| Benzyl Alcohol, | 3 | grams, |
| Potassium Borate | 7.9 | grams or the amount necessary to adjust the pH to 6.3-6.5, |
| Potassium Bicarbonate | 3.4 | grams or the amount necessary to adjust the pH to 6.3-6.5. |

* * * * *